(12) United States Patent
Jean-Ruel et al.

(10) Patent No.: US 10,495,513 B2
(45) Date of Patent: Dec. 3, 2019

(54) MULTI-RESOLUTION OPTICAL SPECTROMETER

(71) Applicant: LightMachinery Inc., Nepean, Ontario (CA)

(72) Inventors: Hubert Jean-Ruel, Ottawa (CA); John Reid, Stittsville (CA); John H. Hunter, Almonte (CA); Jesse Dean, Ottawa (CA); Edward S. Williams, Kanata (CA); Ian J. Miller, Ottawa (CA)

(73) Assignee: LightMachinery Inc., Ottawa, Ontario (CA)

( * ) Notice: Subject to any disclaimer, the term of this patent is extended or adjusted under 35 U.S.C. 154(b) by 0 days.

(21) Appl. No.: 15/873,547

(22) Filed: Jan. 17, 2018

(65) Prior Publication Data
US 2018/0202862 A1 Jul. 19, 2018

Related U.S. Application Data

(60) Provisional application No. 62/447,107, filed on Jan. 17, 2017.

(51) Int. Cl.
| | |
|---|---|
| *G01J 3/26* | (2006.01) |
| *G01J 3/02* | (2006.01) |
| *G01J 3/28* | (2006.01) |
| *G01N 21/25* | (2006.01) |
| *G01J 3/04* | (2006.01) |
| *G02B 26/08* | (2006.01) |
| *G01J 3/18* | (2006.01) |
| *G02B 27/10* | (2006.01) |

(52) U.S. Cl.
CPC ............ *G01J 3/0294* (2013.01); *G01J 3/0208* (2013.01); *G01J 3/0256* (2013.01); *G01J 3/04* (2013.01); *G01J 3/18* (2013.01); *G01J 3/26* (2013.01); *G01J 3/2803* (2013.01); *G01N 21/255* (2013.01); *G02B 26/0808* (2013.01); *G02B 27/1066* (2013.01)

(58) Field of Classification Search
CPC ............ G01J 3/0294; G01J 3/0256; G01J 3/18
See application file for complete search history.

(56) References Cited

U.S. PATENT DOCUMENTS

| 5,969,865 A | 10/1999 | Shirasaki | ................. 359/577 |
| 5,973,838 A * | 10/1999 | Shirasaki | ........... G02B 6/29311 359/577 |

(Continued)

OTHER PUBLICATIONS

"Mode-resolved frequency comb interferometry for high-accuracy long distance measurement" van den Berg et al., Scientific Reports—Sep. 2015.

(Continued)

*Primary Examiner* — Maurice C Smith
(74) *Attorney, Agent, or Firm* — Teitelbaum Bouevitch & McLachlen; Neil Teitelbaum (57) ABSTRACT

The invention relates to a multi-resolution optical spectrometer that employs two output lenses of different focal length to provide a broad wavelength range, coarse resolution spectral measurement and a high resolution, lower range spectral measurement. Light dispersed by a virtual image phase array followed by a diffraction grating in two different dispersion orders may be separately focused by the two lenses upon to 2D detector array to provide the two measurements.

19 Claims, 9 Drawing Sheets

(56) References Cited

U.S. PATENT DOCUMENTS

| | | | |
|---|---|---|---|
| 6,344,910 B1 | 2/2002 | Cao | 398/34 |
| 7,084,985 B2 | 8/2006 | Xie et al. | 356/454 |
| 7,898,656 B2 | 3/2011 | Yun et al. | 356/300 |
| 8,440,952 B2 | 5/2013 | Jalali et al. | 250/208.1 |
| 2005/0046837 A1* | 3/2005 | Izumi | G01J 3/18 356/326 |
| 2006/0012786 A1* | 1/2006 | Goto | G01J 3/04 356/328 |
| 2009/0273777 A1* | 11/2009 | Yun | G01J 3/02 356/300 |
| 2016/0139390 A1* | 5/2016 | Bukshtab | A61B 3/13 351/206 |
| 2017/0082491 A1 | 3/2017 | Stephen et al. | |

OTHER PUBLICATIONS

"Spectrometer Design Guide" Ibsen photonics, May 2013.

* cited by examiner

MULTI-RESOLUTION OPTICAL SPECTROMETER

CROSS-REFERENCE TO RELATED APPLICATIONS

The present invention claims priority from U.S. Provisional Patent Application No. 62/447,107, which is entitled "VIPA spectrometer having multiple spectral resolution ranges", filed Jan. 17, 2017, which is incorporated herein by reference.

TECHNICAL FIELD

The present invention generally relates to optical spectrometers, and more particularly to multi-resolution optical spectrometers that disperse light in two dimensions.

BACKGROUND OF THE INVENTION

High resolution optical spectrometers typically require highly dispersive optical elements. One example of such optical element is a virtually imaged phase array (VIPA), which is an optical component that has a very high angular dispersion $D=d\theta/d\lambda$, where $\theta$ is a dispersion angle at which light of wavelength $\lambda$ is dispersed by the VIPA. A conventional VIPA includes two parallel surfaces, one of which typically has a highly-reflective coating, and the other is partially-reflective. The highly-reflective surface has an input zone 6 that may have an anti-reflection coating through which input light may enter the VIPA at an angle, to be reflected back and forth across a gap between the highly and partially reflective surfaces, gradually leaking out through the partially reflective surface. Because the two reflective surfaces are highly parallel, the output beams have a well-defined phase relationship, which interference in a focal plane of a lens results in a strong angular dispersion that enables the use of the VIPA in a spectrometer.

One limitation of a VIPA is a relatively small free spectral range (FSR), which is typically only about 50-80 times greater than the spectral resolution of the VIPA. If two wavelengths incident on the VIPA are separated by one FSR, their angular locations at the detector will be identical. In order to broaden the overall operating range of the spectrometer beyond one VIPA FSR a second dispersive element in a cross-orientation with the VIPA may be added after the VIPA to allow separation of these otherwise overlapping wavelengths. This second dispersive element could be a dispersing prism or a diffraction grating.

The overall spectral resolution of a VIPA-based spectrometer is defined not only by the spectral resolution of the VIPA, but also by the pixel size of a camera used to detect the dispersed light, the size of the pixel array of the camera, and the focal length of a lens that focuses the dispersed light upon the camera. Typically there is a trade-off between the spectral resolution and the measurement spectral window of the spectrometer, so that a spectrometer with a greater spectral resolution will likely have a narrower measurement spectral window.

Thus there is a need for an optical spectrometer that combines a high spectral resolution with a broader operating wavelength range.

SUMMARY OF THE INVENTION

Accordingly, the present disclosure relates to a spectrometer comprising: a dispersive system comprising two dispersive elements sequentially disposed to disperse input light in two dimensions to produce dispersed light, wherein one of the two dispersive elements has an FSR that is smaller than an operating wavelength range of the spectrometer; one or more detector arrays for detecting the dispersed light; and, two lenses for separately focusing the dispersed light upon the one or more detector arrays; wherein one of the two lenses has a focus distance that is at least 2 times greater than the other of the two lenses.

An aspect of the present disclosure relates to a spectrometer comprising: a dispersive system comprising two dispersive elements sequentially disposed to disperse input light in two orthogonal dimensions to produce dispersed light, wherein one of the two dispersive elements has an FSR that is smaller than an operating wavelength range of the spectrometer; two two-dimensional (2D) detector arrays for detecting the dispersed light; and, two lenses for separately focusing the dispersed light upon the two 2D detector arrays; wherein one of the two lenses has a focus length that is at least 2 times greater than the other of the two lenses. In at least some implementations, the dispersive system is configured to output the dispersed light comprising two light beams corresponding to two different dispersion orders of one of the two dispersive elements, wherein one of the two lenses is disposed in an optical path of one of the two light beams and the other of the two lenses is disposed in an optical of the other of the two light beams at locations wherein the two light beams are at least partially spatially separated, and the two 2D detector arrays are disposed in the focal planes of the two lenses to separately receive the two light beams focused by the respective lenses.

An aspect of the present disclosure provides a spectrometer comprising: first and second 2D detector arrays; a dispersive system comprising a VIPA and a second dispersive element sequentially disposed in an optical path of input light for dispersing thereof in two dimensions, wherein the VIPA is characterized by an FSR that is smaller than an operating wavelength range of the spectrometer, and wherein the dispersive system is configured to output dispersed light comprising first and second light beams corresponding to two different dispersion orders of one of the VIPA and the second dispersive element; and, first and second lenses disposed for separately focusing the first and second light beams upon the first and second detector arrays, respectively; wherein the second lens has a focus distance that is at least 2 times greater than the first lens, so as to provide a greater wavelength resolution in a narrower wavelength band than the first lens.

An aspect of the present disclosure provides a method for analyzing an optical spectrum of input light using a first dispersive element having an FSR that is smaller than a target operating wavelength range of the input light. The method comprises: a) sending the input light onto the first dispersive element that is disposed for dispersing light in a first dispersion direction in accordance with a wavelength content thereof; b) sending the input light onto the second dispersive element that is disposed for dispersing light in wavelength along a second dispersion direction that is generally orthogonal to the first dispersion direction; c) focusing a first portion of the input light dispersed by the first and second dispersive elements in a first dispersion order of one of the first and second dispersive elements upon a first 2D detector array using a first lens; and, focusing a second portion of the input light dispersed by the first and second dispersive elements in a second dispersion order of the one of the first and second dispersive elements upon a second 2D detector array using a second lens that has a greater focus length than the first lens, so as to provide a greater wavelength resolution from the second detector array and a greater wavelength range from the first detector array.

Another aspect of the present disclosure relates to a spectrometer comprising: a dispersive system comprising at least one dispersive element configured to disperse input light to produce dispersed light of two dispersion orders; first and second detector arrays; and first and second lenses disposed to intersect different portion of the dispersed light, wherein the first detector array is disposed in the focal plane of the first lens to detect an illumination pattern of a first of the two dispersion orders, and the second detector array is disposed in the focal plane of the second lens to detect an illumination pattern of the second of the two dispersion orders.

BRIEF DESCRIPTION OF THE DRAWINGS

The invention will be described in greater detail with reference to the accompanying drawings which represent preferred embodiments thereof, in which like elements are indicated with like reference numerals, which are not to scale, and wherein.

DETAILED DESCRIPTION

In the following description, for purposes of explanation and not limitation, specific details are set forth, such as particular circuits, sub-systems, optical and circuit components, mechanical elements, assemblies, or techniques, etc. in order to provide a thorough understanding of the present invention. However, it will be apparent to one skilled in the art that the present invention may be practiced in other embodiments that depart from these specific details. In other instances, detailed descriptions of well-known methods, devices, and tools are omitted so as not to obscure the description of the present invention.

Note that as used herein, the terms "first", "second" and so forth are not intended to imply sequential ordering, but rather are intended to distinguish one element or operation from another unless explicitly stated.

Figure 1:
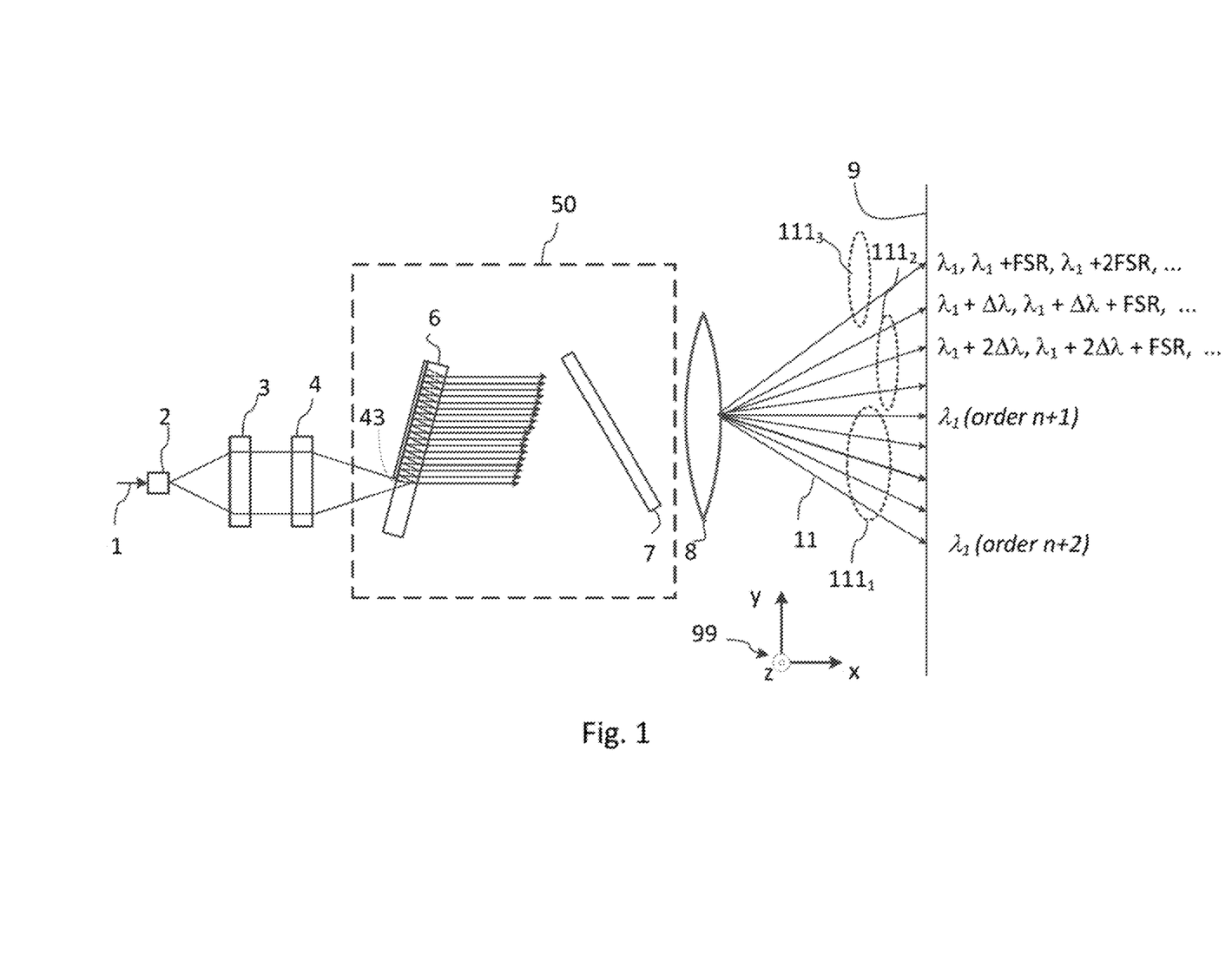
FIG. 1 is a schematic diagram of a VIPA-based optical spectrometer with a single output focusing lens.

With reference to FIG. 1, there is shown a schematic diagram of an example VIPA-based spectrometer. It includes an entrance slit 2 that functions as an input optical port for receiving input light 1; a collimating lens 3; a cylindrical focus lens 4; a dispersion system 50 that includes a VIPA 6 and, in at least some embodiments, a second dispersion element 7, such as a diffraction grating or a prism; a 2D detector array 9, such as a CCD or CMOS camera; and an output focusing lens 8 to focus the light from the dispersive system 50 onto the detector array 9. VIPA 6, which in the shown example is oriented so as to disperse the input light into vertical direction in the plane of the figure, and also the direction of the y-axis of an example Cartesian coordinate system 99, may be coated for a range of wavelengths, for example 400-500 nm, or 500-650 nm, or any other desired wavelength range for which compatible coatings exist. For wavelength ranges extending beyond approximately 1050 nm different detectors may be used in the detector array 9. For example an InGaAs detector array may be used in a spectrometer covering the wavelength range of 1450-1650 nm; a HgCdTe detector array may be used in a spectrometer operating in a wavelength range of 4-5 µm.

Continuing to refer to FIG. 1, in operation the cylindrical focus lens 4 brings the input light 1 passing through the slit 2 to a line focus at the input of VIPA 6, with the line focus extending perpendicularly to the plane of the figure and along the z-axis of the coordinate system 99. The diffraction grating is 7 arranged to disperse the input light at 90° relative to the VIPA dispersion direction (y-axis) in the focal plane of output lens 8; accordingly, grating 7 disperses input light 1 incident thereon along the direction of the z-axis, i.e. perpendicular to the plane of the figure. The function of grating 7 may be understood by noting that any two wavelengths incident on the VIPA 6 that are separated by one free spectral range (FSR) of the VIPA, will appear at the same angular location at the detector 9 in the direction of the VIPA dispersion, i.e. in the plane of the figure; this is illustrated in FIG. 1 by rays 11 and corresponding wavelength identifying notations at the detector 6. A typical VIPA has a relatively small FSR, and the spectrometer may be expected to operate in a wavelength range that is several time broader; by way of example, the finesse of a typical VIPA may be on the order of 70, which means that its FSR is only 70 times greater than the wavelength resolution of the VIPA. The second dispersive element 7 thus functions to spatially separate the wavelengths that are spaced by one or more FSRs of VIPA 6 by dispersing them in a plane that is orthogonal to the plane of the VIPA dispersion, i.e. along z-axis of the (y,z) plane of the coordinate system 99 in the figure.

Figure 2:
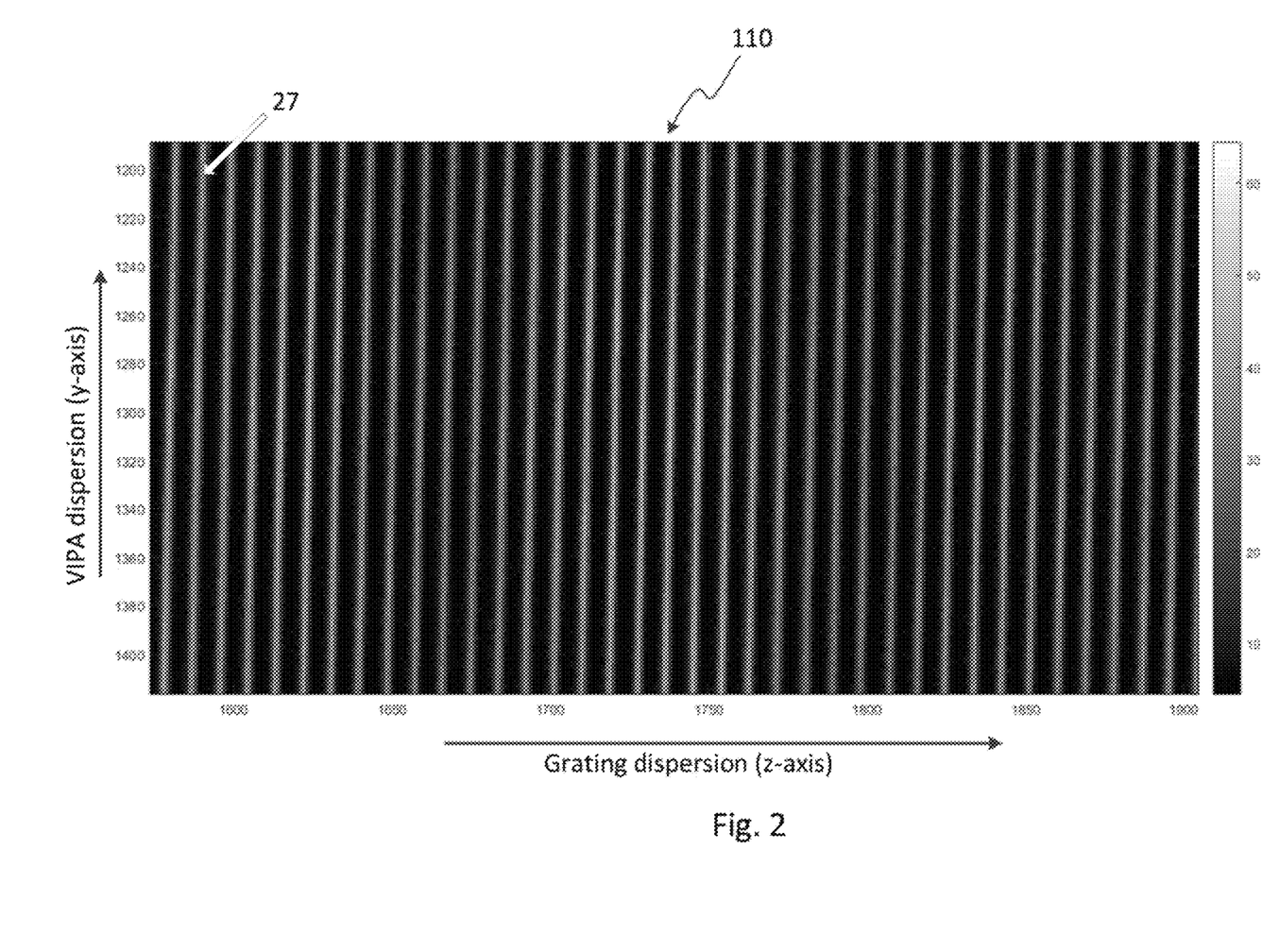
FIG. 2 is an example 2D illumination pattern in a focal plane of the spectrometer of FIG. 1 when illuminated by white light.

Referring to FIG. 2, there is illustrated an illumination pattern 110 that may be formed in the focal plane of lens 8 where the 2D detector array 9 is disposed, which may be a (y,z) plane of the coordinate system 99 of FIG. 1, in response to the spectrometer receiving input light 1 that has a constant spectral density across the operating wavelength range. As can be seen from the figure, illumination of VIPA 6 with a constant spectral density results in a series of bright lines or stripes 27 in the VIPA dispersion direction (y-axis in FIG. 1) alternating with dark bands in the grating dispersion direction (z-axis in FIG. 1). The bright lines 27 may be slightly curved because the VIPA dispersion varies with angle. The lines are also tilted relative to the VIPA dispersion direction because the dispersion of the VIPA is much higher than on the second element. Since the function of the second dispersive element 7 is to spatially resolve wavelengths that are spaced by one FSR of the VIPA, the dispersion $D_2=d\phi/d\lambda$ of the second dispersive element 7 is preferably at least 10 times smaller, and may be 20-40 times smaller than the VIPA dispersion $D_1=d\theta/d\lambda$; here $\theta$ and $\phi$ are angles of dispersion of the input light at the VIPA 6 and at the second dispersive element 7, respectively, due to their respective dispersion properties.

The spectral resolution and the overall bandwidth of the spectrometer of FIG. 1 is determined by the spectral resolution of VIPA 6, grating 7, pixel size of camera 9, array size of camera 9, and the focal length $L_f$ of the output lens 8. Specifically, in the VIPA dispersion direction, one of the limits to the resolution is an equivalent width of one pixel in wavelength space $\delta\lambda_p$. Effectively, the product $P_1$ of VIPA dispersion $D_1$ times the lens focal length $L_f$ times the minimum resolvable wavelength increment $\delta\lambda$, i.e. the wavelength resolution of the spectrometer, should preferably be two to three times as large as the pixel size a of the detector array 9:

$$P_1 = D_1 \cdot L_f \cdot \delta\lambda \cong 2a \ldots 3a. \quad (1)$$

A similar relationship may hold for the grating dispersion direction, where the product $P_2$ of the grating dispersion $D_2$ times the lens focal length $L_f$ times the VIPA FSR $\Delta$ could preferably be select to be of the size of 2 to 10 pixels, or more preferably 4 to 8 pixels:

$$P_2 = D_2 \cdot L_f \cdot \Delta \cong 4a \ldots 8a. \quad (2)$$

The total operating wavelength range $\Delta\lambda$, of the spectrometer under such conditions depends on the number of pixels in the grating dispersion direction $N_{p2}$, and may be given by the expression $$\Delta\lambda = (N_{p2} \cdot a)/(D_2 \cdot L_f) = (N_{p2} \cdot \Delta)/(P_2/a), \quad (3)$$

where $N_{p2} \cdot a = L_z$ is the size of the detector array in the grating dispersion direction. By way of example, if the size of one pixel a≤2 µm, $P_2 \cong 8a$ may be selected in order to fully resolve the bright stripes 27 with minimal cross talk between adjacent stripes. The total operating wavelength range $\Delta\lambda$, of the spectrometer under such conditions may then be given by the number of pixels in the grating dispersion direction $N_{p2}$ times the FSR of the VIPA $\Delta$ divided by 8, $\Delta\lambda$, $=(N_{p2} \cdot \Delta)/8$. Note that equations (1)-(3) assume square or circular pixels for clarity with the same size in the z and y directions; one skilled in the art will however have no difficulty to adopt these equations to elongated pixels.

Thus, for a given combination of VIPA 6, grating 7, pixel size of camera 9, and array size of camera 9, the focal length $L_f$ of the output lens determines both the available resolution and the total wavelength range which can be evaluated with a single exposure. The greater the focal lens, the better is the wavelength resolution of the spectrometer, as $\delta\lambda \sim 1/L_f$ from equation (1). The lower the focal length, the larger the wavelength which can be covered, as evident from equation (3). Lens 8 with a focal length that is too short will limit the performance of the spectrometer either by causing the stripes to overlap, which hinders the unwrapping of the spectrum, or by causing resolvable spectral features to overlap on a single pixel in the VIPA dispersion direction. Thus, for a spectrometer with a given size of the output camera and its pixels, the selection of the output lens 8 involves a trade-off between the spectral resolution and the operating wavelength range.

Figure 3:
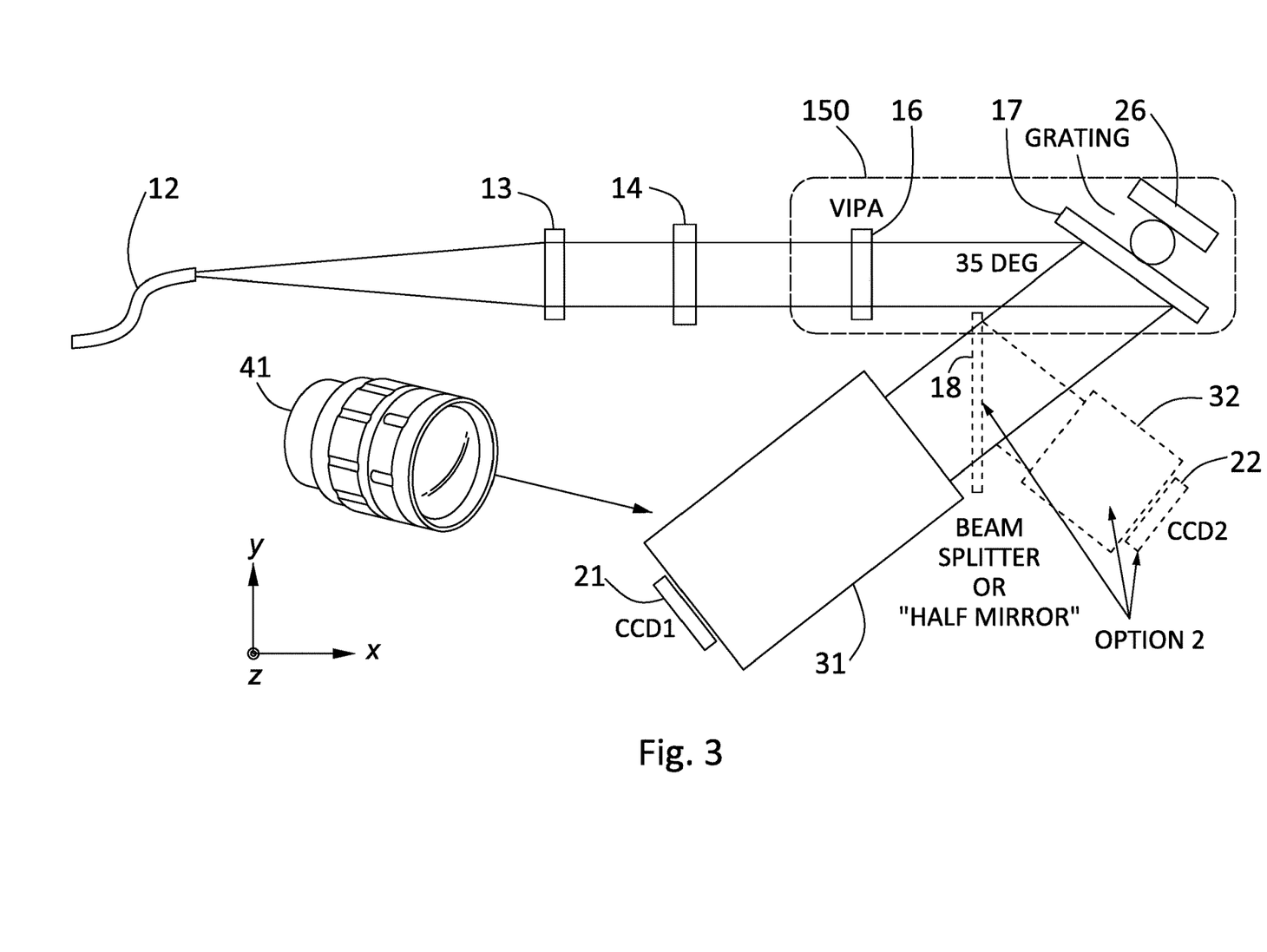
FIG. 3 is a schematic diagram of a multiple resolution VIPA-based optical spectrometer with a zoom lens and/or a semi-transparent mirror and a second lens of a different focus length.

Turning now to FIG. 3, the spectrometer of FIG. 1 may be reconfigured as a multi-resolution spectrometer, in one embodiment by using a zoom lens 41 having an adjustable focus length, for example of the type that is used in photography, as a focusing lens 31 at the output of a dispersive system 150 of the spectrometer. Similarly to the spectrometer of FIG. 1, the spectrometer of FIG. 3 includes an entrance port 12; an input collimating lens 13; a cylindrical focus lens 14, which may bring the light passing through port 12 to a line focus at the input of a first dispersive element 16, which may be embodied as a VIPA 16, a second dispersion element, for example a diffraction grating 17, arranged to disperse the input light at 90° relative to the direction of VIPA dispersion. VIPA 16, which may be coated for a range of wavelengths, for example 400-500 nm, or 500-650 nm or similar, and grating 17 configured to operate in the same wavelength range, form the first and second dispersive elements, respectively, of the dispersive system 150.

The input lenses 13 and 14, VIPA 16, and grating 17 may operate generally as described hereinabove with reference to FIGS. 1 and 2, with lens 31 focusing dispersed light upon a first CCD camera 21, or another suitable 2D detector array, as described hereinabove with reference to FIG. 1. In the illustrated embodiment grating 17 is a reflection grating, but in other embodiments it can be a transmission grating as illustrated in FIG. 1. By way of example, VIPA 16 may have a 60 GHz FSR and may be combined with a 2400 lines/mm grating 17, with the maximum resolution of 1 picometer (pm), for an operating wavelength range centered at 500 nm that can be about 17 nm wide for a 2.6 k pixels wide camera 21, or about 25 nm wide using a 3.9 k pixel wide camera 21. For 2 µm wide pixels, a maximum total spectral range is achieved using a focal length of 12 cm. Given that VIPA 16 and grating 17 can both function over a much broader range than 17-25 nm, it would be advantageous to expand this range whenever desired or simultaneously with also providing a high resolution, narrow spectral range mode. In an ultimate expanded-range, coarse-resolution mode where the VIPA resolution does not need to be achieved and the grating spectral resolution may be sufficient, the spectrum can be reconstructed based only on the dispersion of grating 17, such that the stripes 27 from the grating dispersion do not need to be resolved.

Continuing to refer to FIG. 3, in one embodiment the multi-resolution, multi-range operation may be achieved with the illustrated spectrometer by using zoom lens 41 as the output lens 31 that focuses the dispersed light from the dispersive system 150 onto the first camera 21. In a high-resolution, lower range mode the adjustable zoom lens 41 may be set to have a longer focus length for maximum resolution, which depends on the characteristics of the VIPA 16, but which could for example be in the range of 0.5 pm to 3 pm, or more generally in the range 0.2 pm to 10 pm, and possibly in the range between 0.1 pm to 30 pm. In a lower resolution wide-range mode the zoom lens 41 may be set to a shorter focal length, for example so as to provide a coarse wavelength resolution of approximately 0.5+\−0.2 FSR of VIPA 16, which may equate to approximately 35 pm for an example VIPA 16; this short-focus setting will provide an increased measurement spectral range, which by way of example may be approximately 125000 times greater than the highest resolution of the spectrometer in the high-resolution mode. The focus length ratio of zoom lens 41 between the highest resolution mode and the lowest resolution mode may be in the range of 2 to 50, or more narrowly 5 to 20, providing an equivalent wavelength resolution ratio between the modes. Advantageously, the zoom lens 41 may also be set to provide a range of intermediate wavelength resolution/measurement spectral range combinations between the two extreme modes.

The operating wavelength range is often expressed as a multiple of the spectrometer's finest wavelength resolution. In the case of a resolution of 1 pm, a wavelength range of 10 nm would equate to 10 000 times coverage. Preferably, with the high resolution setting of the zoom lens, the wavelength coverage may be between 5000 and 15000 times the maximum resolution. A more general wavelength range of 3000 to 30000 times resolution may also be realized, and possibly a range as small as 1000 times or as large as 60000 times the maximum resolution. In some embodiments when the zoom lens is set for low resolution, the observable resolution may be approximately 20-30 times lower than in the high resolution setting, but the wavelength range would proportionally increase to 75000-125000 times the instruments highest resolution. More generally a wavelength range between 50000 and 150000 times the maximum resolution would be obtained with the low resolution setting. In the low resolution setting, the wavelength range could be as little as 30000 times the instrument's highest resolution or as much as 200000 times the instrument's highest resolution. All of these values will scale with the resolution achievable by the VIPA 16 provided the diffraction grating 17, and imaging optics are scaled appropriately.

Continuing to refer to FIG. 3, a second embodiment may employ two output lenses, lens 31, which in this embodiment may be a fixed-focus lens and may be referred to as the first lens, and a second lens 32, which may also be a fixed-focus lens and have a second 2D detector array 22, such as a second CCD camera, disposed in its focal plane. In one embodiment first lens 31 may have the long focus length to provide a high spectral resolution and a narrow spectral range operation similar to the long focus length setting of the zoom lens 41 in the first embodiment described above, and second lens 32 may have the short focus length to provide the low spectral resolution and a broad spectral range operation similar to the short focus length setting of the zoom lens 41 in the first embodiment described above. In another embodiment the first and second lenses 31, 32, and the first and second cameras 21, 22 coupled thereto, may interchange. A beam-splitter 21, such as a partially transparent mirror, with a beam splitting ratio of for example 90/10, or closer to 50/50 in other implementation, may be positioned between the two lenses 31 and 32 to split the dispersed light from grating 17 into two beams. In one embodiment the long focal length lens, for example lens 31, may receive the greater fraction of the dispersed light, for example approximately 90%. The ratio of the focal lengths of the first and second lenses 31, 32 may be greater than 2:1, preferably 5:1 or greater, and more preferably 10:1 or greater.

Both the first and second embodiments of the spectrometer of FIG. 3 may use an adjustable grating mount 26, which may rotate to enable changing the center wavelength on the high resolution camera 31 so as to select different portions of the overall spectral range of the spectrometer. With the addition of the rotatable grating mount 26, the broad range, low resolution view of the input spectrum provided by the second camera 22 coupled to the short-focus lens 32 can be used to identify spectral areas of interest, and to gauge the rotation of the grating 17 for zooming into the selected spectral areas with the long-focus lens 31 and camera 21 coupled thereto.

Referring now back to FIG. 1 for illustration, each input wavelength may appear in several dispersion orders in the VIPA dispersion direction in the focal plane of lens 8. The number of orders which are illuminated depends on the range of angles present in the input light incident upon the VIPA's input port or area 43. As the angular range of the incident light increases, additional orders may be illuminated on the output side 9. In FIG. 1, wavelength $\lambda_1$ is shown to appear in the focal plane of lens 8 in dispersion orders of the VIPA n, n+1, and n+2, with wavelength $\lambda > \lambda_1$ appearing in-between. Groups of rays of different wavelengths corresponding to these three different dispersion orders of the VIPA at the output of lens 8 are schematically indicated at beams $111_1$, $111_2$, and $111_3$. Thus, light dispersed by VIPA 6 of FIG. 1, or VIPA 16 of FIG. 3, may be comprised of two or more groups of rays that correspond to different VIPA dispersion orders in the focal plane of lens 8 and which are dispersed by the VIPA in differing angular ranges. Similarly, the second dispersion element 7 may also disperse light incident thereon in different dispersion orders, which in the case of a dispersion grating may be referred to as diffraction orders. As a result, the dispersed light at the output of the dispersive system 50 or 150 may be viewed as composed of two or more light beams generally corresponding to different dispersion orders of the first and second dispersive elements, e.g. a VIPA and a grating, as they appear in the focal plane of the output lens, with each input wavelength present in each of these beams. Note that a dispersion order generally corresponds to a path delay between interfering beams measured in a number of wavelengths; while the grating dispersion order m will likely to be low, e.g. m=1, 2, or 3, the dispersion order n of a VIPA is likely to be a large integer number.

Figure 4:
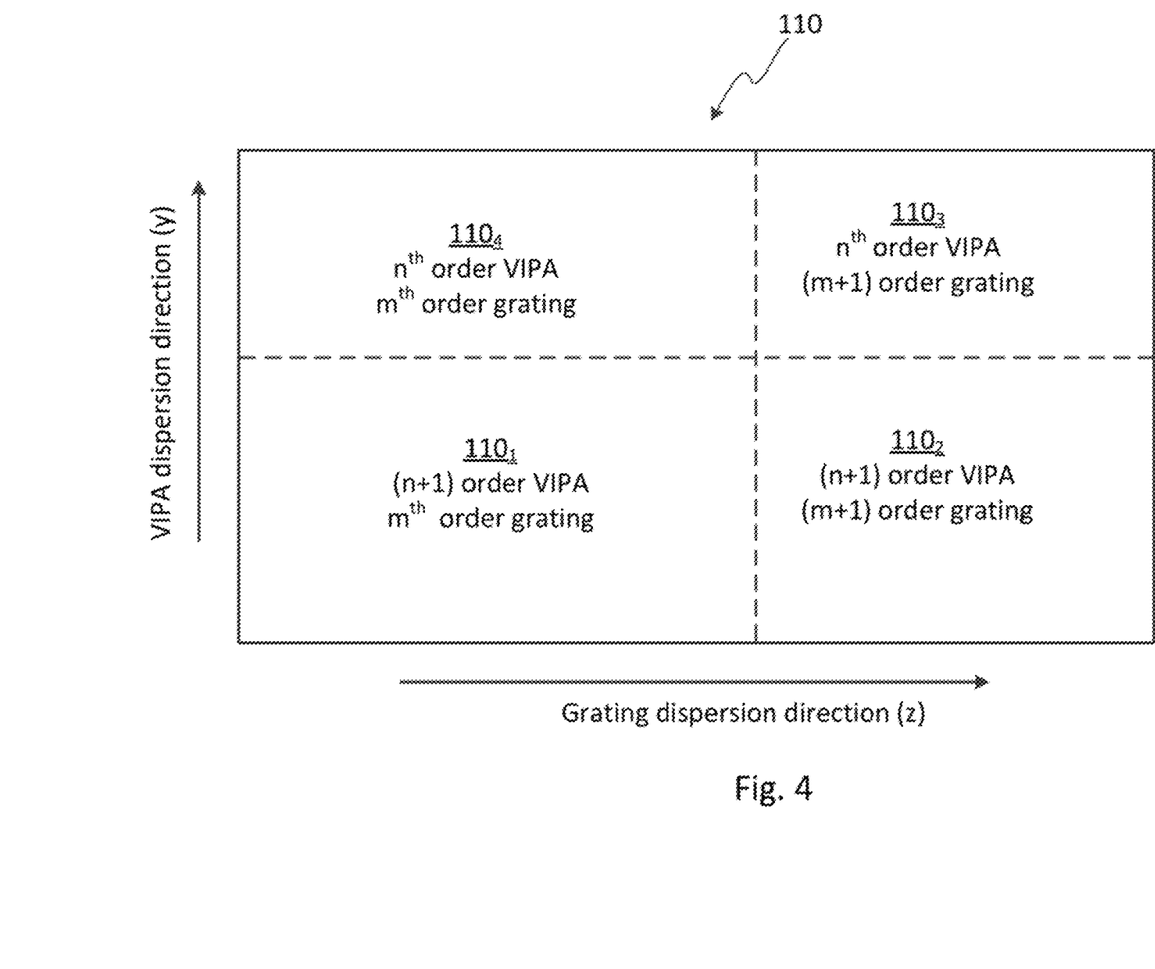
FIG. 4 is a schematic diagram of the illumination field in the focal plane of an output lens of a VIPA-based spectrometer encompassing multiple dispersion orders of the VIPA and grating.

Referring to FIG. 4, it schematically illustrates example locations $110_1$-$110_4$ of illumination patterns of different dispersion orders of VIPA 6 and grating 7 in the focal plane of lens 8 having an aperture suitable to receive two dispersion orders of each VIPA 6 and grating 7. Generally each one of these four illumination patterns represents the spectrum of the input signal with a similar spectral resolution, within a factor of 2, and any one of them could be used for full spectral analysis with a resolution and in a spectral window defined by the output lens. However, a simultaneous multi-resolution measurement of the input light may be performed by selectively focusing light beams which produce the illumination patterns of different dispersion order using lenses of different focus lengths.

Figure 5:
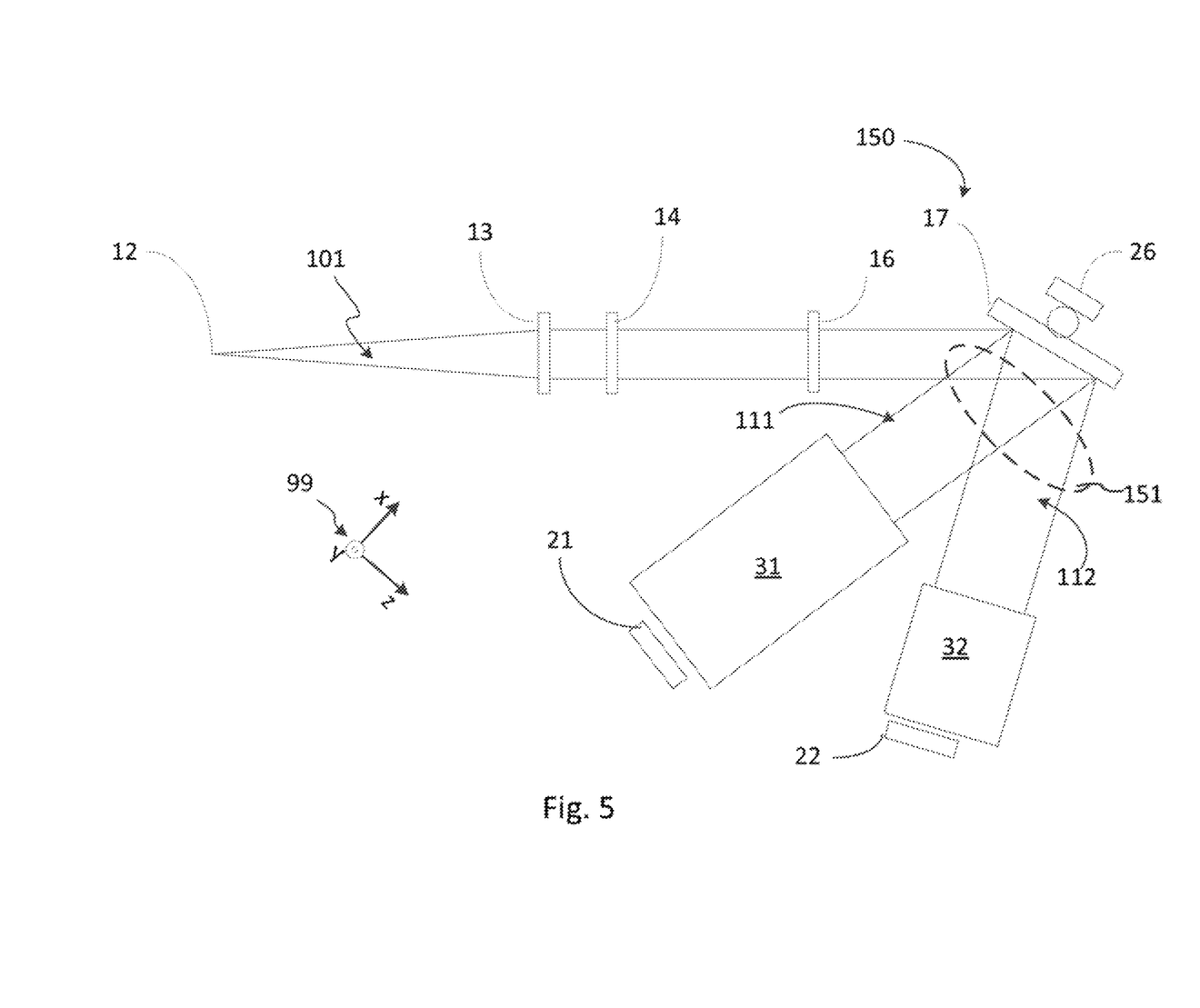
FIG. 5 is a schematic perspective view of a dispersive system of a multiresolution dual-lens VIPA-based spectrometer with a reflector for separating beams corresponding to different diffraction orders of the grating.

Referring to FIG. 5, there is illustrated a modification of a multi-resolution spectrometer of FIG. 3 in which the first and second output lenses 31, 32 are disposed to separately receive two different spatial portions of the dispersed light 151 that generally correspond to two different dispersion orders of the dispersive system 150. Although light forming the different dispersion orders may not be completely separated spatially other than in a focal plane of a lens, the lenses 31, 32 may be positioned where overlap is small, for example less than 50%, or preferably less than 10% in power. In the illustrated embodiment dispersed light 151 at the output of grating 17 is schematically shown to be composed of two light beams 111 and 112 that contain fractions of input light 101 which, when focused by a lens after propagating through the dispersive system 150, would produce patterns corresponding to two different dispersion orders of the diffraction grating 17; by way of example, beam 111 may contain the light corresponding to the first dispersion order of grating 17, while beam 112 may contain the light corresponding to the second order of grating 17, or any order higher than the dispersion order of light in beam 111. These beams propagate in somewhat different directions or angular ranges and get at least partially separated at some distance from the grating. The first lens 31 is disposed in an optical path of the first light beam 111 and the second lens 32 is disposed in an optical of the second light beam 112, preferably at locations where the two light beams are at least partially spatially separated, and each of the lenses predominantly receives light of the corresponding dispersion order, preferably with no more than 50%, and preferably less than 10% in power, of cross-coupling of the light that would produce a pattern of the other of the two dispersion orders. In one implementation the first lens 31 may be a long-focus lens and produces a spectral image of the input light upon the first detector array or camera 21 with a high spectral resolution but in a relatively narrow spectral window, as described hereinabove with reference to FIG. 3, with the center wavelength of the spectral window defined by the orientation angle of grating 17. The second lens 32 may be a short-focus length lens with parameters as described hereinabove with reference to FIG. 3, and produces a spectral image of the input light 101 at the second detector array or camera 22 with a lower spectral resolution but in a much broader spectral range than that produced by the first lens 21. In another implementation the positions of the short focus length lens 32 and the long focus length lens 31 may be interchanged. Since light dispersed in a higher order may experience somewhat greater angular dispersion than that dispersed by the same dispersive element in the lower order, it may be advantageous to use the lens with the longer focus length with the higher-order beam to provide the greatest spectral resolution. By way of example, in one implementation the first beam 31 may be formed predominantly of light of the first dispersion order of grating 17 and is received by lens 31 with the greater focus length, while the second beam 32 may be formed predominantly of light of the second dispersion order of grating 17 and is received by lens 32 with the shorter focus length. The ratio of the focus lengths of the long focus length lens and the short focus length lens that may embody the first and second lenses 31, 32 in the spectrometer of FIG. 5 may be generally as described hereinabove with reference to FIG. 3.

In the embodiment of FIG. 5 the spatial separation of the dispersed light into light portions, or beams, which in a focal plane form interference patterns of different order is performed by using lenses 31, 32 of a suitably small aperture which can only capture a desired spatial portion of the dispersed light corresponding mostly to one dispersion order. In other embodiments one or more partial beam splitters could be used to further separate spatial portions of light output from the second dispersive element corresponding to different dispersion orders.

Figure 6:
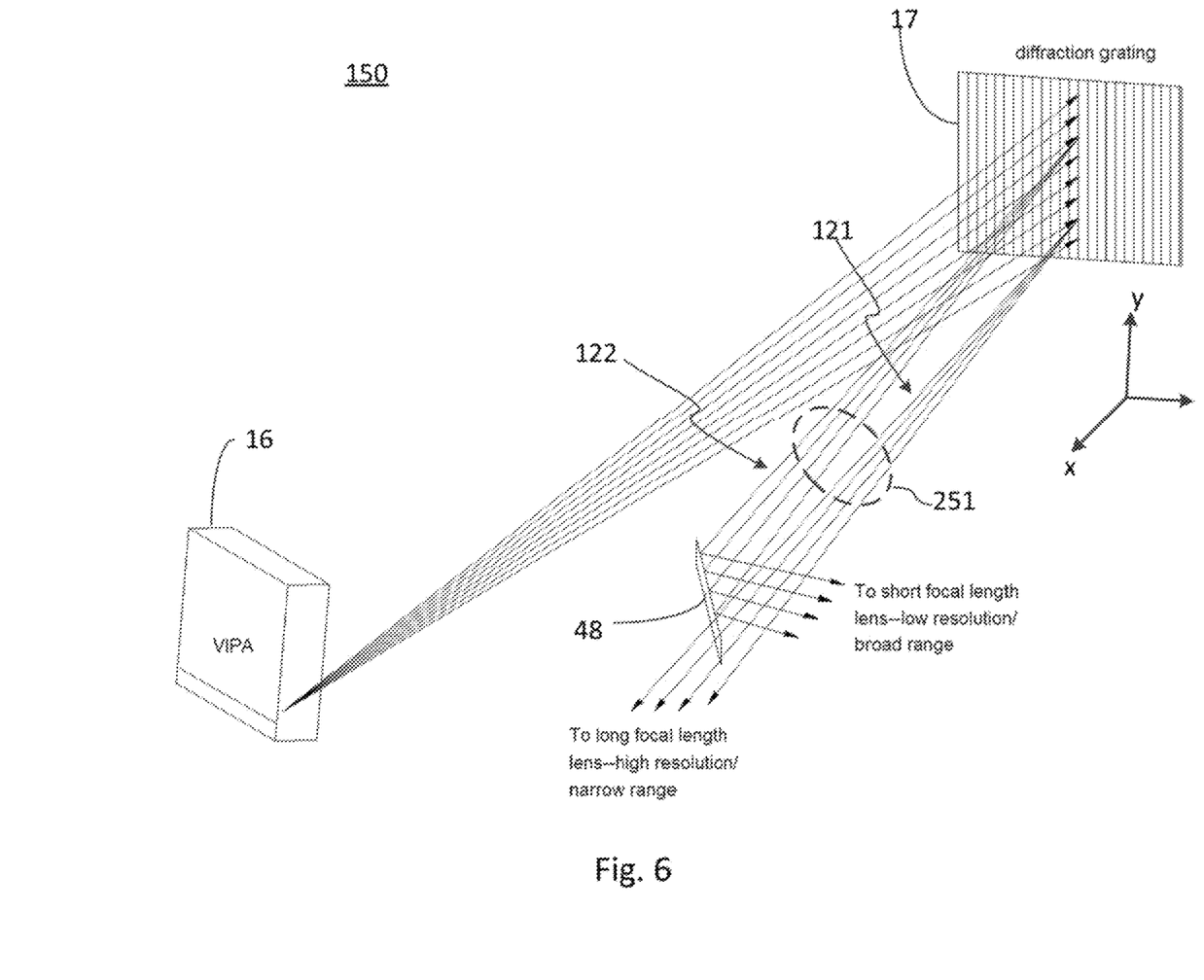
FIG. 6 is a schematic diagram of a multiresolution dual-lens VIPA-based spectrometer with two lenses of different focus lengths receiving beams of different dispersion orders of the VIPA.

Turning now to FIG. 6, an example partial beam splitting arrangement is schematically illustrated in the context of an embodiment wherein a partial-size reflector 48 is used to split out a portion of the output light 251 of the dispersion system 150 corresponding to a particular dispersion order of VIPA 16. An embodiment of the dispersion system 150 is illustrated here in a shown here in a perspective view, in which light corresponding to different dispersion orders of VIPA 16 may be seen. As illustrated, the dispersion system 150 outputs dispersed light 251 that would form patterns of two different dispersion orders of VIPA 16 in a focal plane of a lens, with corresponding groups of rays, or beams, which are indicated at 121 and 122 and which relate to the two different VIPA orders. Partial-size reflector 48, which may be for example in the form of a highly reflective mirror, is disposed so as to intersect only a spatial portion of the dispersed light, i.e. beam 122, that predominantly corresponds to the higher VIPA dispersion order. The reflected light may then be focused by the short focus length lens, such as lens 32 of FIG. 5, to produce upon detector array 22, as also shown in FIG. 5, a spectral image of input light across a broad operating wavelength range of the spectrometer with a coarse resolution as defined by the focus length of that lens. The remaining spatial light portion or beam 121, which may contain predominantly light corresponding to the lower VIPA order, passes by reflector 48 to the long focus length lens, such as lens 31 of FIG. 5, to produce a high-resolution spectral image in a relatively narrow spectral window, which may be scanned across the operating wavelength range covered by the short-focus lens by rotating grating 17. Because mirror 48 is not at the focal plane of a lens, a small portion of light that would produce a pattern of the higher VIPA order may also be intercepted by the mirror, thereby reducing the intensity of the high-resolution image. However, mirror 48 may be positioned at a location where less than 50%, and preferably less than 10% of the intercepted light may be of the wrong dispersion order, so that the associated loss does not significantly reduce the performance of the high resolution channel. In other embodiments light of the lower VIPA order may be selectively split off from the dispersed light, and either one of the two long-focus lens and the short-focus lens can be used to form an imager of either of the two VIPA orders.

Figure 7:
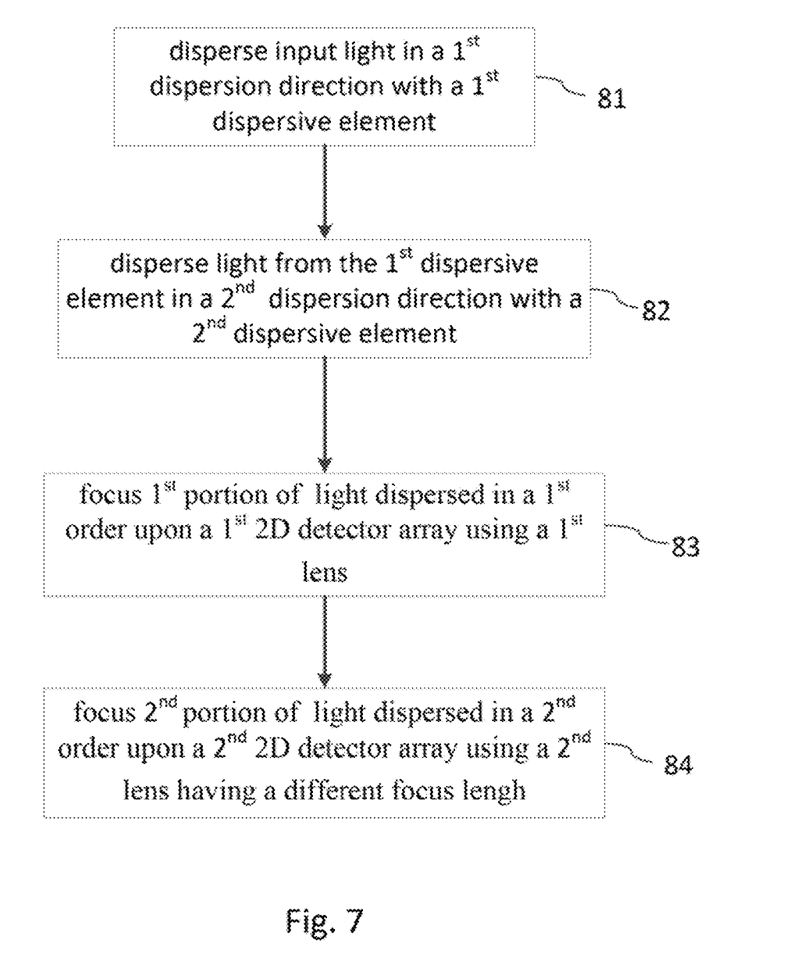
FIG. 7 is a flowchart of a method for multi-resolution spectrum measurements using two orthogonal dispersive elements and multiple lens for separately focusing beams corresponding to different dispersion orders.

Thus an aspect of the present disclosure provides a method for analyzing an optical spectrum of input light will now be described with reference to FIG. 7.

At step 81, the input light is dispersed with a first dispersive element in a first dispersion direction in accordance with a wavelength content thereof; in at least some embodiments the first dispersive element, such as a VIPA 16, may have an FSR that is smaller than a target operating wavelength range; this method. At step 82, the input light dispersed by the first dispersive element is sent onto a second dispersive element that is disposed for dispersing light in wavelength along a second dispersion direction that may be generally orthogonal to the first dispersion direction. At step 83, a first portion of the input light dispersed by the first and second dispersive elements in a first dispersion order of one of the first and second dispersive elements is focused upon a first two-dimensional (2D) detector array using a first lens. At step 84, which may be concurrent with step 83, a second portion of the input light dispersed by the first and second dispersive elements in a second diffraction order of the one of the first and second dispersive elements is focused upon a second 2D detector array using a second lens that has a greater focus length than the first lens, so as to provide a greater wavelength resolution in a relatively smaller spectral window from the second detector array, and a greater wavelength range with a lower spectral resolution from the first detector array.

Figure 8:
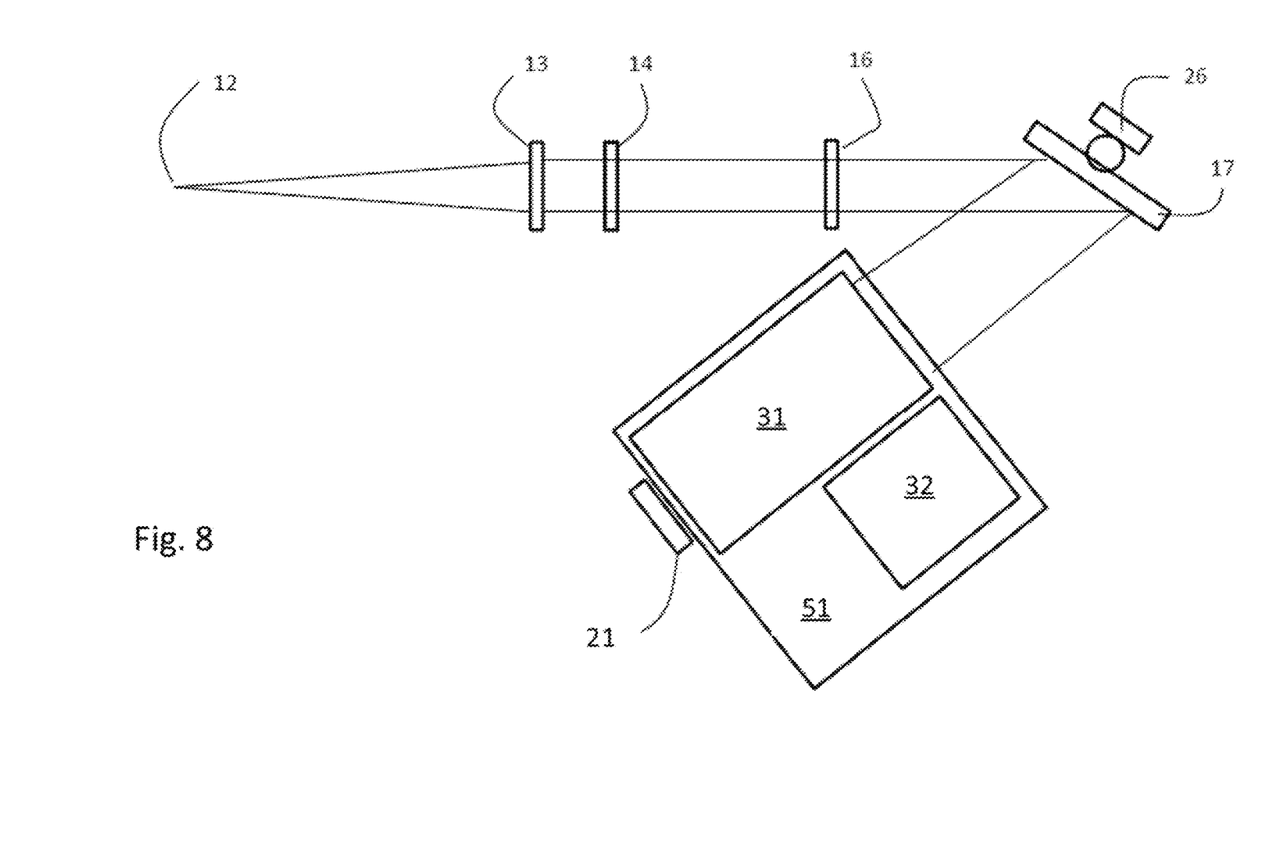
FIG. 8 is a schematic diagram of a multiresolution dual-lens VIP-based spectrometer with two lenses of different focus lengths on a movable mount.
Figure 9:
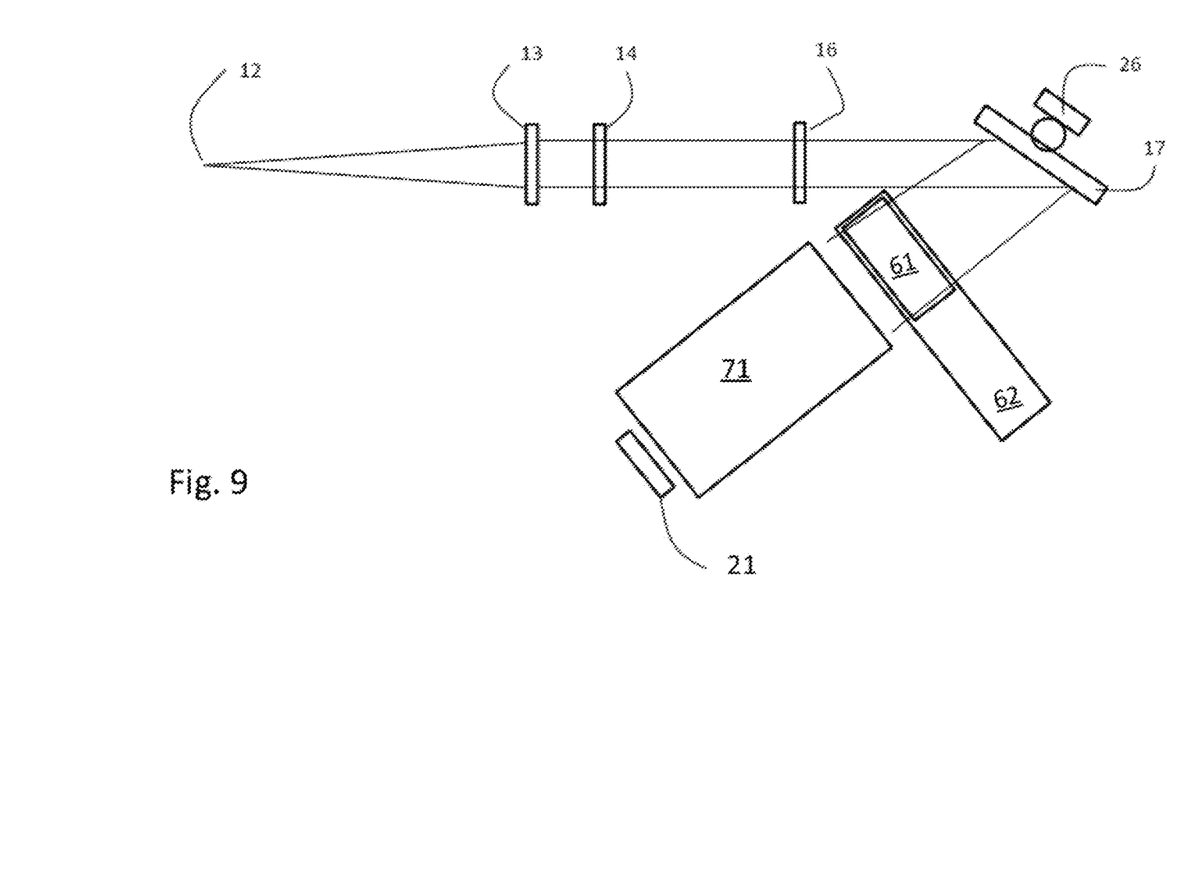
FIG. 9 is a schematic diagram of a multiresolution single-lens VIP-based spectrometer with an insertable beam expender.

With reference to FIGS. 8 and 9, in some embodiments lenses or lens systems of different focus length may be used sequentially in time rather than concurrently. FIG. 8 illustrates an embodiment in which lenses 31, 32 of different focal lengths are disposed upon a movable mount 51, such as a bayonet mount for example, to be interchangeably inserted in the optical path of light dispersed by VIPA 16 and grating 7 to allow alternating between the high resolution and broad wavelength range modes of operation. In this embodiment the spectrometer may be made more compact and only requires a single camera 19, however only a single-resolution measurement may be performed at a time.

FIG. 9 illustrates a variation in which an in-line beam expander 61, such as for example a Galilean telescope, may be inserted in the path of the dispersed beam to modify the focal length of an output lens 71. The beam expander 61 may be moveable, e.g. capable of being slid or rotated, into position between grating 17 and the output lens 71 on a moveable platform 62. The beam expander 61 decreases the input angles by the same ratio as the beam expansion, thus increasing the wavelength range detected by the camera 19 by the same ratio as the beam expander 61.

In various embodiments described hereinabove a recalibration of the spectrometer after changing the zoom lens setting, or the grating rotation, may be performed by measuring a known spectrum, for example from a mercury lamp, or some other lamp with a suitable spectrum. A motorized rotation stage, combined with automatic identification of spectral features from the calibration source, would enable rapid adjustment of center wavelength of the spectrometer.

Table 1 provides exemplary ranges of several parameters that may be relevant to one or more of the described embodiments, which are however not limited by these ranges.

TABLE 1

|  | In general | In particular |
| --- | --- | --- |
| Wavelengths | 150 to 20000 nm | 400 to 700 nm |
| Camera pixel sizes | 1 to 20 μm | 1.5 to 5 μm |
| Camera array size | 0.1 to 14 MP | 5 to 10 MP |
| VIPA thickness | 0.1 to 20 mm [Resulting FSR range for wavelengths from 150 to 20000 nm: 0.20 pm to 4.3 μm] | 0.34 to 3.4 mm [Resulting FSR range for wavelengths from 400 to 700 nm: 16 to 491 pm] |
| Focal length of basic (high-resolution mode) lens | 25 to 5000 mm | 50 to 500 mm |
| Ratio of the basic (high resolution mode) lens' focal length and the effective focal length producing the low resolution mode | 1:2 to 1:30 | 1:2 to 1:10 |
| Grating rotation angle (grating normal with respect to the incident light) | −80 to 80° | 40 to 80° |
| Grating groove density | 300 to 3600 l/mm | 600 to 2400 l/mm |

It will be appreciated that the term 'lens' as used herein encompasses single lenses as well as lens systems composed of two or more lens elements.

The above-described exemplary embodiments are intended to be illustrative in all respects, rather than restrictive, of the present invention. Thus the present invention is capable of many variations in detailed implementation that can be derived from the description contained herein by a person skilled in the art. For example, each of the example embodiments described hereinabove may utilize other optical elements; in other embodiments functions of two or more optical elements may be combined in a single component. Furthermore, although the example embodiments are described hereinabove with reference to a VIPA as a first dispersive element, other embodiments may utilize other dispersive elements in its place, such as but not limited to a regular Fabry-Perot etalon, an echelle grating. Similarly, embodiments may be envisioned where the second dispersive element 17 is not a diffraction grating but for example a prism, or any other suitable dispersive element, wherein or the second dispersive element 17 is absent altogether from the spectrometer; in the latter case the detector arrays 21, 22 may be one-dimensional, such as e.g. a linear array of suitable photodiodes. Furthermore, elements or features that are described hereinabove with reference to a particular example embodiment may also relate to other described embodiments. All such and other variations and modifications are considered to be within the scope and spirit of the present invention as defined by the following claims.

We claim:

1. A spectrometer comprising:
   a dispersive system comprising two dispersive elements sequentially disposed to disperse input light in two dimensions to produce dispersed light, wherein one of the two dispersive elements has a free spectral range (FSR) that is smaller than an operating wavelength range of the spectrometer;
   one or more detector arrays for detecting the dispersed light; and,
   two lenses for separately focusing the dispersed light upon the one or more detector arrays;
   wherein one of the two lenses has a focus distance that is at least 2 times greater than the other of the two lenses.

2. The spectrometer of claim 1 wherein one of the two dispersive elements has an angular dispersion that is at least 10 times greater than the other of the two dispersive elements.

3. The spectrometer of claim 2 wherein the one of the two dispersive elements comprises at least one of a virtually imaged phase array (VIPA), an echelle grating, or a Fabry-Perot etalon, and the other of the two dispersive elements comprises at least one of a prism or a diffraction grating.

4. The spectrometer of claim 2 wherein:
   the dispersive system is configured to output the dispersed light comprising two light beams corresponding to two different dispersion orders of one of the two dispersive elements,
   wherein one of the two lenses is disposed in an optical path of one of the two light beams and the other of the two lenses is disposed in an optical path of the other of the two light beams at locations wherein the two light beams are at least partially spatially separated, and
   the one or more detector arrays comprise two detector arrays disposed to separately receive the two light beams focused by the two lenses.

5. The spectrometer of claim 4 wherein the one of the two lenses with the longer focal length is disposed in the optical path of one of the two light beams that corresponds to a greater dispersion order than the other of the two light beams.

6. The spectrometer of claim 4 comprising a reflector disposed in the optical path of one of the two light beams and out of the optical path of the other of the two light beams so as to further spatially separate the two light beams prior to the two lenses.

7. The spectrometer of claim 1 including a beam splitter disposed in an optical path of the dispersed light to split the dispersed light into the first and second light beams, wherein one of the two lenses is disposed in an optical path of one of the two light beams and the other of the two lenses is disposed in an optical of the other of the two light beams, and wherein the one or more detector arrays comprise two detector arrays disposed to separately receive the two light beams focused by the two lenses.

8. The spectrometer of claim 1 including a mount movably holding the two lenses for interchangeably inserting either one of the two lenses in an optical path of the dispersed light.

9. The spectrometer of claim 3 wherein the one of the two dispersive elements comprises the VIPA, comprising an input port for receiving the input light, and one or more input lenses disposed to bring the input light to a line focus at the VIPA.

10. The spectrometer of claim 9, wherein the other of the two dispersive elements comprises the diffraction grating disposed optically following the VIPA to disperse the input light in a direction that is generally orthogonal to a VIPA dispersion direction.

11. A spectrometer comprising:
first and second two-dimensional detector arrays;
a dispersive system comprising a virtual image phase array (VIPA and a second dispersive element sequentially disposed in an optical path of input light for dispersing thereof in two dimensions, wherein the VIPA is characterized by a free spectral range (FSR) that is smaller than an operating wavelength range of the spectrometer, and wherein the dispersive system is configured to output dispersed light comprising first and second light beams corresponding to two different dispersion orders of one of the VIPA and the second dispersive element; and,
first and second lenses disposed for separately focusing the first and second light beams upon the first and second detector arrays, respectively;
wherein the second lens has a focus distance that is at least 2 times greater than the first lens, so at to provide a greater wavelength resolution in a narrower wavelength band than the first lens.

12. The spectrometer of claim 11 comprising an input port for receiving the input light, and one or more input lenses disposed to bring the input light to a line focus at the VIPA.

13. The spectrometer of claim 12, wherein the second dispersive element comprises at least one of: a dispersion grating and a prism that is oriented with a dispersion direction that is generally orthogonal to a VIPA dispersion direction.

14. The spectrometer of claim 13 wherein the second dispersive element optically follows the VIPA.

15. The spectrometer of claim 11 including a reflector disposed in an optical path of one of the first and second light beam so as to further separate the first and second light beams.

16. The spectrometer of claim 11 including a reflector disposed in an optical path of one of the first and second light beams so as to further separate said light beams at the first and second lenses.

17. The spectrometer of claim 11 wherein one of the first and second lenses is disposed to receive a portion of the input light that is dispersed by the VIPA in a first dispersion order, and the other of the first and second lenses is disposed to receive light that is dispersed by the VIPA in a second dispersion order.

18. The spectrometer of claim 11 wherein one of the first and second lenses is disposed to receive a portion of the input light that is dispersed by the second dispersive element in a first dispersion order, and the other of the first and second lenses is disposed to receive light that is dispersed by the second dispersive element in a second dispersion order.

19. A method for analyzing an optical spectrum of input light using a first dispersive element having a free spectral range (FSR) that is smaller than a target operating wavelength range, the method comprising:
sending the input light onto the first dispersive element that is disposed for dispersing light in a first dispersion direction in accordance with a wavelength content thereof;
sending the input light onto the second dispersive element that is disposed for dispersing light in wavelength along a second dispersion direction that is generally orthogonal to the first dispersion direction;
focusing a first portion of the input light dispersed by the first and second dispersive elements in a first dispersion order of one of the first and second dispersive elements upon a first two-dimensional (2D) detector array using a first lens; and,
focusing a second portion of the input light dispersed by the first and second dispersive elements in a second diffraction order of the one of the first and second dispersive elements upon a second 2D detector array using a second lens that has a greater focus length than the first lens, so as to provide a greater wavelength resolution from the second detector array and a greater wavelength range from the first detector array.

* * * * *